United States Patent [19]
Bonavent et al.

[11] 4,351,642
[45] Sep. 28, 1982

[54] ELEMENTS SENSITIVE TO CERTAIN POLLUTING AGENTS, PARTICULARLY HYDROCARBONS AND METHOD OF USE

[75] Inventors: Gérard Bonavent, Rueil-Malmaison; Lucien Montabord, Cormeilles en Parisis, both of France

[73] Assignee: Institut Francais du Petrole, Rueil-Malmaison, France

[21] Appl. No.: 143,979

[22] Filed: Apr. 28, 1980

[30] Foreign Application Priority Data

Apr. 27, 1979 [FR] France .................................. 79 10786

[51] Int. Cl.³ ..................... G01N 33/00; G08B 21/00; H01H 35/00
[52] U.S. Cl. ............................... 23/230 M; 23/230 L; 23/232 R; 73/61.1 R; 200/61.04; 210/924; 340/604; 340/605; 422/68; 422/88; 423/245
[58] Field of Search ............ 23/230 R, 230 L, 230 M, 23/232 R; 422/83, 68, 69, 88; 73/61.1 R; 338/34; 525/241, 333, 338; 423/245; 210/924; 340/603, 604, 605; 200/61.04, 61.05, 61.06

[56] References Cited
U.S. PATENT DOCUMENTS

| | | | |
|---|---|---|---|
| 2,604,423 | 7/1952 | Slotterbecke et al. | 428/335 |
| 3,470,340 | 9/1969 | Hakka | 200/61.04 |
| 3,518,183 | 6/1970 | Evans | 210/924 X |
| 3,720,797 | 3/1973 | Gunn et al. | 73/61.1 R UX |
| 3,766,295 | 10/1973 | Crossland et al. | 525/241 X |
| 3,970,863 | 7/1976 | Kishikawa et al. | 340/605 X |
| 4,058,802 | 11/1977 | Meyers | 73/61.1 R X |
| 4,125,822 | 11/1978 | Perren et al. | 23/230 L X |

Primary Examiner—Arnold Turk
Attorney, Agent, or Firm—Millen & White

[57] ABSTRACT

A sensitive element which deteriorates when contacted with the polluting agent, this material comprising a sequenced styrene-butadiene copolymer, of which at least a part is hydrogenated.

These elements can be used in pollution sensing devices, or for constituting at least a wall portion of a container housing a product for fighting against pollution.

19 Claims, 2 Drawing Figures

ELEMENTS SENSITIVE TO CERTAIN POLLUTING AGENTS, PARTICULARLY HYDROCARBONS AND METHOD OF USE

BACKGROUND OF THE INVENTION

The present invention relates to elements sensitive to certain polluting organic compounds, in particular hydrocarbons, but also to some halogenated organic products, such as chloroform, trichlorethylene, allyl-chloride, and to oxygenated solvents, such as acetone and its derivatives, certain alcohols, and the like.

These elements are in particular suitable to form part of devices which comprise at least one element formed of a deteriorable material or, more generally, of a material whose mechanical characteristics are modified in contact with the polluting product.

These elements are, for example, pollution sensors wherein a pollution sensitive element is located in the area where pollution should be detected, for example in the vicinity of a pipe, on the surface of a body of water, or also in the atmosphere, this element co-operating with means adapted to actuate a visual and/or sound alarm when the sensitive element is deteriorated by the polluting product.

The invention is also applicable to automatic devices for fighting against pollution by putting into operation a suitable absorbing or neutralizing agent in the solid (powder), liquid or gaseous state. In such devices, the deterioration of a sensitive element upon contact thereof with the polluting agent will release the antipollution product.

However reference will be more particularly made in the following to the first indicated application, i.e. to the construction of pollution sensors, more specifically of devices capable of detecting the presence of polluting products, such as hydrocarbons, particularly on the surface of a water body.

The problem of pollution by hydrocarbons is indeed very important for everybody.

It is difficult, if not impossible, and always very expensive, once pollution is already present, to try fighting against its noxious and sometimes irreversible consequences.

A preventing action is necessary. Harbour equipments, refineries, airports, distribution circuits, require automatic pollution sensing devices which are both sensitive and reliable, to permit prevision of the steps to be taken when pollution is threatening.

This requires a system which is positioned at the locations where risks of leakage are found, or at places where hydrocarbons may flow.

This system must be adapted to remain at the same location in operative condition over a sufficient time interval, for example three months, so that its maintenance is not too burdensome, and to detect at any time the presence of hydrocarbons.

The problem to be solved is as follows:
1°/—At sea:
(a)—Detection of hydrocarbons in case of accident, so as to follow the evolution of the hydrocarbon layers.
(b)—Detection of fraudulous hydrocarbon discharging.
2°/—In a refinery:
(a)—Detection of the presence of hydrocarbons in the cooling circuits, in the settling tanks, before discharging waste waters into water streams,
(b)—Detection of hydrocarbon leakage from pipelines, fuel storage tanks, etc...

There already exist automatic detection devices sensitive to certain polluting products, such as hydrocarbons, which comprise two sections of a strip or thread interconnected by means of a special glue which is deteriorated or dissolved by the polluting agent.

The assembly being kept under tension, the action of the polluting agent causes breaking of the assembly, thus triggering an alarm signal. Such devices have been for example manufactured by the Canadian Company Bennett Pollution Controls Ltd, under the name "Oil Spill Detection System".

Such a system is however difficult to produce and the results thereof are not very reliable, since the sensitivity of the gluing to the polluting agents highly depends on the quality of fabrication.

There also exist devices based on the use of a solid sensitive element, which, when contacted with polluting products becomes swollen or is destroyed, thereby causing the triggering of an alarm, as described in French Patent Application No. 2 178 950, German Patent Application Nos. 1 910 166 and 2 434 914 and Swiss Pat. No. 411 633.

The various products proposed heretofore to constitue the sensitive element are not fully satisfactory, either because they are not sensitive enough to the polluting products (as in the device of French Pat. No. 2 178 950), or, when sensitive enough, they cannot withstand for a sufficient time the action of light (as in the devices described in French Patent Application No. 2 254 749 and German Patent Application No. 2 434 914).

The invention provides a solid sensitive element which does not suffer from the above-indicated drawbacks.

DETAILED DISCUSSION

More precisely, the sensitive element according to the invention is made of a material which deteriorates when contacted with the polluting products and comprises a sequenced styrene-butadiene copolymer of which at least a part is hydrogenated.

According to further embodiments of the invention, this material may contain stabilizing agents with respect to ultra-violet rays, anti-oxidants and 400K oil in respective proportions to be determined according to the intended utilization.

The sensitive element according to the invention may have any shape, for example it may consist of a thin band, whose partial or complete destruction by the polluting products will, for example, generate a visual and/or sound alarm signal, an electric signal, or the like.

The sensitive element may also form a portion of a container wall housing a pollution-fighting product, this wall portion being adapted to open by itself when contacted with the polluting product, by degradation of the material constituting this wall.

Figure 1:
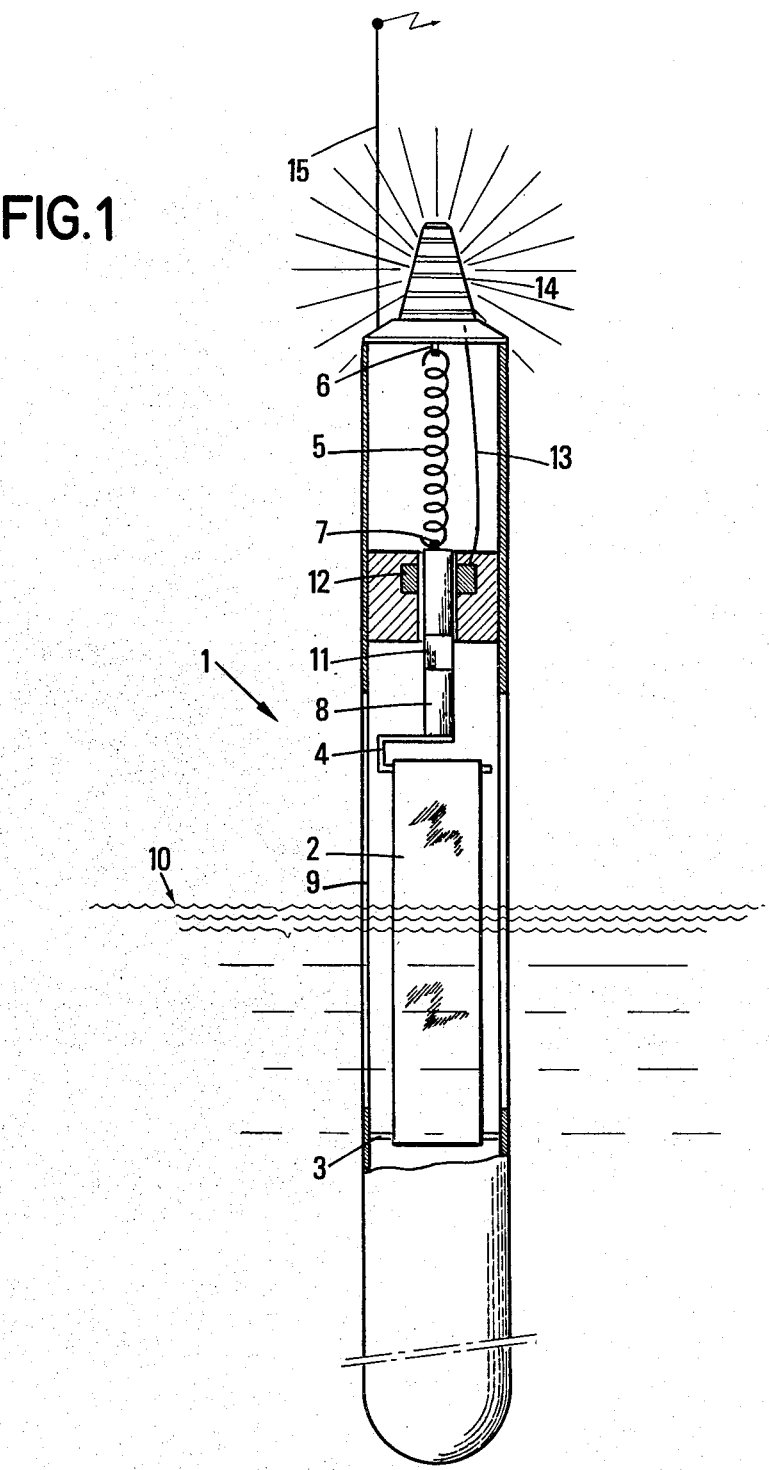
FIG. 1 is an illustration of a floating hydrocarbon detection device according to the invention.

FIG. 1 diagrammatically shows, by way of example, a hydrocarbon sensing device 1 floating on the water surface. This device is maintained in a substantially vertical position by weighting means at its lower part. The illustrated arrangement is shown by way of example.

Within this device a thin strip 2 made of a material according to the invention is connected at one end thereof to securing means 3, its other end being connected to a securing lug 4. A spring 5, having one end 6 connected to the upper part of the device and its other end 7 connected to the securing lug 4 through an elongate member 8, maintains the strip 2 under tension.

The device is widely open at 9 to permit hydrocarbons 10, spread over the water surface, to come into contact with the strip 2.

The elongate member 8 carries a magnetic mass 11 which, when the strip 2 is broken as the result of its deterioration by the hydrocarbons in contact therewith, is brought, by a return spring 5, to a position facing a magnetic sensor 12, thereby actuating, through the electrical conductor 13, a sound and/or electric alarm 14 located at the top of the device and/or transmitting a radio signal from an aerial 15.

The strip 2, made of a material which is selectively attacked by hydrocarbons, thus acts as a "fuse" which breaks under the action of hydrocarbons spread over the water surface and then actuates a warning system.

Figure 2:
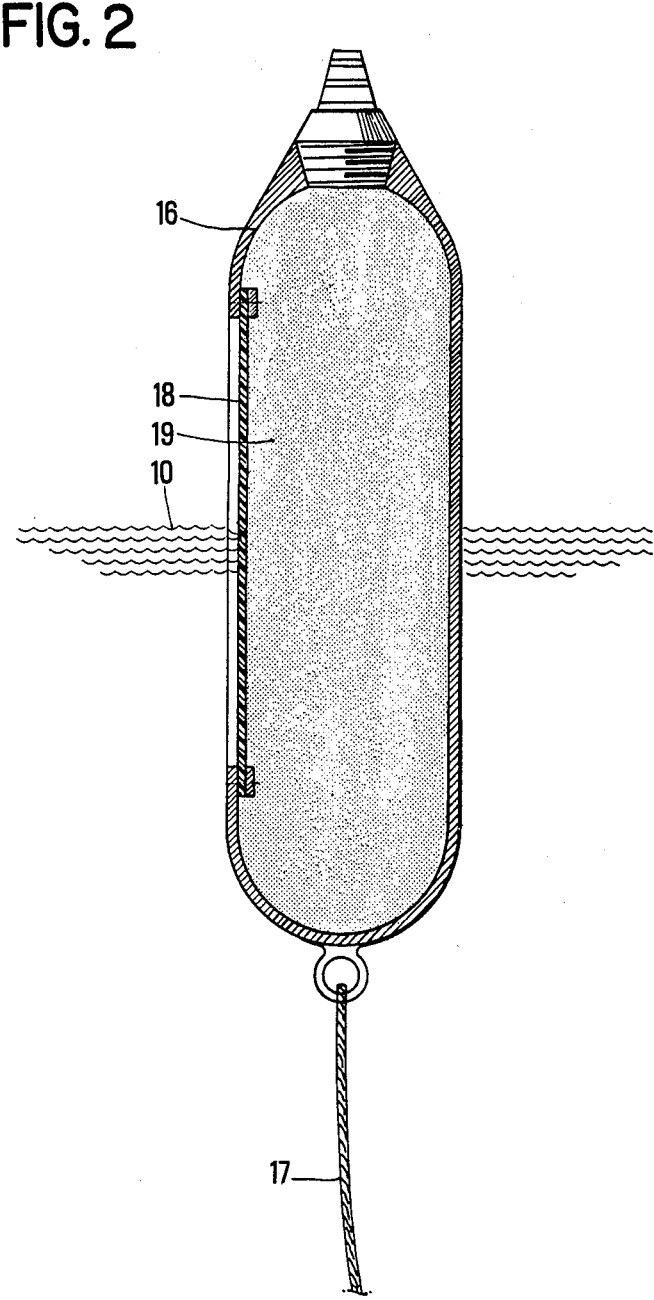
FIG. 2 is an illustration of another embodiment of the invention wherein an antipollutant is released upon contact of the detector with a pollutant.

FIG. 2 shows an alternative embodiment of the sensitive element of the invention. A film of at least partially hydrogenated sequenced styrene-butadiene copolymer forms at least one wall portion 18 of a container 16 housing an anti-pollution product 19. When the film contacts a pollutant 10, e.g., a hydrocarbon, on the surface of the water, the film deteriorates and the anti-pollution product is released.

Tests have been performed with different types of materials constituting the strip 2 which has been manufactured in the form of a calibrated film 20 to 25 centimeters long, 4 cm wide and of a determined thickness of at least 50 microns.

The films have been tested by taking into account the expected environment for hydrocarbon pollution sensors, i.e. by checking on the one hand the film resistance with respect to reference hydrocarbons, and on the other hand its resistance to natural ageing means, i.e. sun rays, air, water and temperature cycles.

The tests consisted of determining the life time of films maintained under tension in a given physico-chemical medium. The film is folded on itself to form a loop which is positioned on a support member (aluminum rod) and which carries a 150 grams weight. This assembly is placed in a tank containing water so that the interface between water and air is at equal distances from the support member and the weight.

The so-formed assembly may be exposed to the heat of sun rays and thus subjected to daily thermal cycles, in an opaque housing, protected from light, or in a suitable tank for tests of resistance to hydrocarbons.

The tests with the hydrocarbons are achieved by depositing onto the water surface a relatively small amount of hydrocarbons.

In this way both sides of the film are wet and thus offer the maximum area to the action of hydrocarbons.

A crude oil has been selected to simulate detection of hydrocarbons at sea: Arabian Light topped at 150° C., designated by the reference (BAL 150).

Gas-oil and kerosene have been selected for detection of tank leakages.

Kerosene represents pollution in airports or leakage in the cooling water used in refineries.

Tests on the various materials have been carried out in the following different media:
1°/—Water only (reference)
2°/—Water+(BAL 150)
3°/—Water+Gas oil
4°/—Water+kerosene.

These tests have been so devised as to determine the resistance of a given material to a homogeneous liquid and/or to two immiscible liquids. In the case of two immiscible liquids, the determination of the sensitivity of the material is difficult because it is not easy to form, for example, a very thin layer (less than one tenth of a millimeter) of crude oil or gas oil on the water surface since the hydrocarbon cannot be spread evenly.

Current tests are performed with hydrocarbon layers of a thickness lower than 1 millimeter, thus the attack of the material occurs over an area smaller than 16 $mm^2$.

Using fluid hydrocarbons of low viscosity and small interfacial tension—such as kerosene and to a lower extent gas oil—it is possible to obtain on the water surface a hydrocarbon layer having a thickness of about 1/10 mm, provided a detergent is used to improve the wetting. With the reference crude oil (BAL 150) which is very viscous at such a small thickness, the layer will not spread.

The compositions used for the material constituting the sensitive element are of two types. The first type comprises the compositions based on a sequenced styrene-butadiene copolymer, as already known from the prior art, the second type of compositions according to the invention comprising a sequenced styrene-butadiene copolymer of which at least a part is hydrogenated, i.e. which comprises a mixture of sequenced styrene-butadiene copolymer with hydrogenated sequenced styrene-butadiene copolymer.

1. COMPOSITIONS BASED ON SEQUENCED STYRENE-BUTADIENE COPOLYMER (COMPARISON)

The strip 2 has been formed as a thin film of a sequenced styrene-butadiene copolymer of the type commercially sold as a mixture with siliceous charges, such as CARIFLEX MT 710-3 (Registered Trade Mark of SHELL). Owing to its hydrocarbon nature, this material is highly sensitive to hydrocarbons and has a high resistance to water.

A laboratory method has been used to manufacture the film quantities necessary for the tests. The above-indicated product being not, up to now, commercially available as a film, it is not possible to used an industrial technique for manufacturing films, such as a calendering or extrusion-inflation process which would require huge amounts of raw material (from a few hundred kilos to many tons). Thus only the two conventional laboratory techniques have been considered, i.e. casting of a solution on a glass plate and compression moulding between two metal plates.

The pellets of the commercial product are dissolved, under stirring, into trichlorethylene, in a ratio of 400 $cm^3$ of solvent for dissolving 100 g of solid product.

The solution is then cast onto a glass plate, using a conventional device called a filmograph. The thickness of the solution (and hence of the film) is adjusted by the filmograph. It is thus possible, without any difficulty, to form films of a thickness ranging from 50 to more than 200 microns.

The so-obtained films are 200 mm broad. The evaporation of the solvent enabling stripping of the film from the mould requires a few hours.

After this stripping, the films are sprinkled with talc to prevent them from sticking to one another, then they are cut into strips of a 4 cm width and a 20 to 25 cm length.

In the case where charges and additives should be incorporated into the polymer it is necessary to achieve mixing in a roller mixer before dissolving in trichlorethylene. Dispersion of the charges and additives in trichlorethylene (or in the solution of polymer in trichlorethylene) is not very good and pellets are formed which do not become wet.

The mechanical dispersion of the fine solid particles is better achieved by the mechanical action of the rolls. Charges and stabilizing compounds are incorporated to the polymer at 130° C. on the rolls of the mixer. In this way the solution and the finished product, i.e. the film, are homogeneous.

Mould Release or Stripping

Stripping of the so-formed CARIFLEX film is not very easy. Utilization of an external stripping agent (a silicone oil) was not satisfactory because the obtained film was corrugated. It was then devised to use an internal stripping or mould release agent which would act both as a plasticizer and optionally as an agent of compatibility with the hydrocarbons which must wet and dissolve the film.

The first internal stripping agent used was BAL 150 with which various mixtures have been achieved to determine the optimum quantity to be introduced into the CARIFLEX. The intended goal was to provide a material which in addition to its aptitude to an easy stripping or mould release would show a high fracility to the action of BAL 150. Thus the time of breaking has been determined for these compositions. The results of the tests are reported in Table 1 below.

TABLE 1

| | PROPORTIONS OF BAL 150 IN THE CARIFLEX | | | | |
|---|---|---|---|---|---|
| | 1% | 2% | 4% | 8% | 16% |
| Breaking time in BAL 150 | 12 mn | 14 mn | 10 mn | 6 mn 20 s | 2 mn 20 s |

The above tests concern films of a 60 to 70 microns thickness under a load of 150 g. With 16% BAL 150, the CARIFLEX gives a very interesting response time.

Moreover since the evolution of the characteristics of a topped crude oil was not known a 400K oil (i.e. 400 Koweit, a designation used by Mobil Oil Company) was substituted for BAL 150 as stripping agent. This oil consisting of a hydrocarbon base, an antioxidant and a detergent, was used in a proportion of 20% in CARIFLEX, which gave the formulation LM 2.147.2 reported in Table 2, this table indicating the different formulations of the material.

Stabilization with Respect to Light

It has been ascertained that the preceding formulation is very sensitive to light (Table 2). Within 24 hours the film deteriorates by action of light, while its life time reaches 5 weeks in the dark. In order to stabilize this material, two types of products have been used: opaque charges and stabilizing agents with respect to ultra-violet rays, with the addition of anti-oxidants.

Charges of various nature have been used, such as graphites, carbon blacks and white charges, such as calcium carbonate and titanium oxide.

The additives were the following:
anti-oxidants: amines, such as β-naphthylamine, phenolic anti-oxidants sold under the trade-mark IRGANOX, or esters, such as dilauryl dipropionate (D L D P);
stabilizers with respect to ultra-violet rays: organostannic compounds, such as the commercial products TINUVIN and IRGASTAB.

TABLE 2

| PRODUCTS REFERENCES | LM 2 147.2 | LM 2 149.2 | LM 2 154.1 | LM 2 155.1 | LM 2 155.2 | LM 2 156.1 | LM 2 158.1 | LM 2 159.1 | LM 2 159.2 |
|---|---|---|---|---|---|---|---|---|---|
| CARIFLEX | 100 | 100 | 100 | 100 | 100 | 100 | 100 | 100 | 100 |
| "400 K" oil | 20 | — | 20 | 20 | 20 | 20 | 20 | 20/10 | 20 |
| HAF Black | — | 4 | — | — | — | — | — | 13 | — |
| ART Black | — | — | 10 | — | — | — | — | — | — |
| MT Black | — | — | — | — | — | 10 | 10 | — | — |
| Ca CO$_3$ | — | — | — | 40 | — | — | — | — | — |
| Ti O$_2$ | — | — | — | — | 30 | — | — | — | — |
| β naphthylamine | — | 1.4 | — | — | — | 1 | — | — | — |
| Tinuvin P | — | — | — | — | — | 1.5 | 2.5 | — | — |
| Tinuvin 327 | — | — | — | — | — | — | 2.5 | 0.5 | 2 |
| Tinuvin 770 | — | — | — | — | — | — | — | 0.5 | 2 |
| Irgastab | — | — | — | — | — | — | 2.5 | — | — |
| Irganox | — | — | — | — | — | — | 2 | — | — |
| Irganox 1010 | — | — | — | — | — | — | — | 0.3 | 1.2 |
| DLDP | — | — | — | — | — | — | 2 | 0.3 | 1.20 |
| Thickness (microns) | 75 | — | 73 | 69 | 69 | 65 | 82 | 95 | 100 |
| Breaking (grams) | 1052 | — | — | — | — | — | — | — | — |
| Life time in: | | | | | | | | | |
| light | <24 hrs | — | <24 hrs | <24 hrs | 24 hrs | 51 hrs | <24 hrs | <54 hrs | <54 hrs |
| dark | >5 weeks | — | — | — | — | — | — | — | 3 months |
| BAL 150 | 6mn 38 s | — | — | — | — | — | — | — | — |
| gas oil | 25 s. | — | — | — | — | — | — | — | — |
| kerosene | — | — | — | — | — | — | — | — | — |

Graphites have been selected because it was thought that their lamellar structure would be effective for a good protection of a thin film, since it might be assumed that during the moulding operation the particles would form successive strata over the depth. Two graphite types have been selected on the basis of the sedimentation characteristics of the product, since the particles should remain in suspension throughout the mass, without settling during evaporation of the solvent.

Different mixtures have been made using this product by varying the amount of black substance. The presence of small quantities of black substance made it possible to double the life time of the product compared to the formulation without a charge, but the life times remain short: about 2 days only.

The addition of "white" charges (formulation LM 2.155.1) or of titanium "white" (formulation 2.155.2) was not more successful. In all these cases a life time of one or two days is not satisfactory.

The darkening action of the charges was combined with the chemical action due to ultra-violet resistant agents (Tinuvin) and to anti-oxidants (naphthylamine, Irganox, etc. . . ). Also these tests were not successful. Other formulations (2.158.1 and 2.159.1) did not bring any progress. In all these cases the samples deteriorate and many cracks appear in the part of the strip 2 in contact with air (the submerged part remains unaltered). It is thus apparent that the destruction phenomenon occurs in the air.

Tests performed in the dark by using two formulations (LM 2.147.2 uncharged, and LM 2.159.2 charged and doped) has shown that the rapid destruction is mainly caused by light, since in the dark the life time reaches or exceeds three months for the charged formulation, whereas it is only about fifty hours in the light.

The use of CARIFLEX TR MT 710 3 has thus only proved deceptive in the preparation of formulations withstanding the light, which is important for applications in refineries, in harbours or at sea. The structure of the polymer gives it a high sensitivity to hydrocarbons—sensitivity of polystyrene fractions and of butadienestyrene fractions—but is too sensitive to light, this sensitivity being further increased owing to the necessity of employing thin films.

2. COMPOSITIONS BASED ON HYDROGENATED SEQUENCED STYRENE-BUTADIENE POLYMER

As hydrogenated sequenced styrene-butadiene copolymer a hydrogenated CARIFLEX TR commercially available in the USA under the trade name KRATON G. 1652 has been selected. This material was used as basic polymer for the different formulations described in Table 3 which gives the results of the tests.

TABLE 3

| REFERENCES | LM 2 171.1 | LM 2 171.2 | LM 2 170.2 | LM 2 174.1 |
| --- | --- | --- | --- | --- |
| KRATON G 1652 1652 | 100 | 100 | 100 | 85.7 |
| CARIFLEX TR MT 710 3 | — | — | — | 14.3 |
| Oil 400 K | — | 20 | 20 | 20 |
| Black MT | — | — | 10 | 10 |
| Tinuvin 770 | — | — | 1 | 1 |
| D L P D | — | — | 0.6 | 0.86 |
| Irganox 1010 | — | — | 0.6 | 0.86 |
| Irgastab | — | — | — | 0.86 |
| Polyethylene + black | — | — | 2 | — |
| Thickness (microns) | 80 | 100 | 110 | 95 |
| Resistance (grams) (for 40 mm width) | 13000 | 8800 | 4000 | 3649 |

TABLE 3-continued

| REFERENCES | LM 2 171.1 | LM 2 171.2 | LM 2 170.2 | LM 2 174.1 |
| --- | --- | --- | --- | --- |
| Life time in: | | | | |
| kerosene | 11 s | | 10 s | 10 s |
| gas oil | 1mn 33 s | | | 1mn 30 s |
| BAL 150 | 12mn 10 s | 11mn 41 s | 14mn | 10mn 5 s |
| light | >1 year | >1 year | >1 year | >1 year |

The following films have thus been produced always by pouring solutions into trichlorethylene:
- a film of the commercial product KRATON G 1652 (formulation LM 2.171.1)
- a film of the commercial product KRATON G 1652 plasticized with 400K oil (formulation LM 2.171.2)
- a film of the commercial product KRATON G 1652 charged with black and with stabilizing substances (formulation LM 2.170.1)
- a film wherein KRATON G 1652 is admixed with CARIFLEX TR MT 170 3 (formulation LM 2.174.1), i.e. which comprises a sequenced styrene-butadiene copolymer of which at least a part is hydrogenated.

The formulations charged with additives are prepared in the same manner as with CARIFLEX, by incorporating, on the roller mixer, charges into the polymer, then dissolving the mixture in oil-containing trichlorethylene. In the case of KRATON G 1652 the temperature of the rollers was set at 200° C., so as to start gelifying the polymer. In the presence of air a degradation of the final product could be expected. Thus it was preferred to make use of an intermediary mixture of easier fabrication, based on CARIFLEX at a lower temperature of 130° C. Accordingly the following steps were carried out:
- incorporation of the stabilizing agents and of the black substance into CARIFLEX at 130° C. on a roller mixer,
- dissolution of this mixture with KRATON G 1652 into trichlorethylene,
- dissolution of oil into this solution and casting of the film.

The film LM 2.174.1 was prepared in this way.

The thin films-about 100 microns thick-have an instantaneous mechanical resistance higher than that of CARIFLEX films (from 1 to 4 kg/mm$^2$, as compared with 0.3 to 0.7 kg/mm$^2$). The Young's modulus is also higher.

The behaviour in the reference hydrocarbons is very satisfactory for the four formulations.

Resistance to light appears from now on more than satisfactory, since the four formulations have been exposed to solar radiation for more than one year without showing any failure.

There has thus been prepared in the laboratory a product of high sensitivity to light and heavy hydrocarbons and which retains the larger part of its mechanical characteristics, in the shape of a thin film, when exposed to solar radiation, and this over 1 year time. Such a material is thus adapted to constitute fuses in hydrocarbon pollution sensors.

For manufacturing fuses on an industrial scale, the more rational method may be to proceed by extrusion inflation so as to obtain a circular sheath which, by simple cutting, for example every 4 cm, will produce ready-for-use fuses.

Such a material is sensitive to hydrocarbons (it can be destroyed within less than 10 minutes and even less than 1 minute of their contact, according to the nature of the hydrocarbons) and not very sensitive to light, and has good mechanical characteristics. It is therefore possible to use it for manufacturing containers (bags of suitable size, for example) for cleaning products (absorbents, detergents, etc...) for putting these products more easily into operation than by spreading or sprinkling, the latter methods being sensitive to the wind.

It must be also noted that this material can be used for detecting chemical pollution, particularly by solvents, which give this product other applications than fighting against hydrocarbon pollution.

We claim:

1. A sensitive element comprising
   (a) a component made of a material which is resistant to sunlight but which deteriorates upon contact with an organic pollutant, and
   (b) means for generating a countermeasure, said means cooperating with said component and being actuated upon deterioration thereof; wherein said material comprises a sequenced styrene-butadiene copolymer of which at least a part is dehydrogenated.

2. A sensitive element according to claim 1, wherein said material contains 400K oil.

3. A sensitive element according to claim 1, wherein said material includes stabilizing agents with respect to ultra-violet rays.

4. A sensitive element according to claim 1, wherein said material includes anti-oxidants.

5. A sensitive element according to claim 1, wherein said countermeasure comprises a signal.

6. A sensitive element according to claim 1, wherein said component is a film 50–200 microns thick.

7. A method for detecting an organic pollutant, comprising placing a sensitive element according to claim 1 in a location where the presence of said pollutant is to be detected.

8. A sensitive element according to claim 1, wherein said component constitutes at least one wall portion of a container housing an anti-pollution product; and wherein said countermeasure comprises the release of said product.

9. A method of treating organic pollutants, comprising placing a sensitive element according to claim 8 in a location where an organic pollutant is present to contact said component thereby releasing said anti-pollution product.

10. A method according to claim 7 or 9, wherein said pollutant is a hydrocarbon.

11. A sensitive element according to claim 1, wherein a part but not all of said copolymer is hydrogenated.

12. A sensitive element according to claim 11, wherein said copolymer comprises about 86% by weight of hydrogenated styrene-butadiene copolymer and about 14% non-hydrogenated styrene-butadiene copolymer.

13. A sensitive element according to claim 12, wherein the copolymer further contains 400K oil, carbon black, an anti-oxidant and an ultra-violet stabilizer.

14. A component suitable for use in a sensitive element comprising (a) a component which deteriorates upon contact with an organic pollutant, and (b) means for generating a countermeasure, said means cooperating with said component and being actuated upon deterioration thereof; said component being a film 40–200 microns thick and made of a material which is resistant to sunlight and which comprises a sequenced styrene-butadiene copolymer of which at least a part is hydrogenated.

15. A component according to claim 14, wherein said film is about 100 microns thick.

16. A component according to claim 14, in the form of a wall portion for a container housing an anti-pollution product.

17. A component according to claim 14, wherein said copolymer is partly but not completely hydrogenated.

18. A component according to claim 17, wherein said copolymer comprises about 86% by weight of hydrogenated styrene-butadiene copolymer and about 14% non-hydrogenated styrene-butadiene copolymer.

19. A component according to claim 18, wherein the copolymer further contains 400K oil, carbon black, an anti-oxidant and an ultra-violet stabilizer.

* * * * *

UNITED STATES PATENT AND TRADEMARK OFFICE
CERTIFICATE OF CORRECTION

PATENT NO. : 4,351,642
DATED : September 28, 1982
INVENTOR(S) : Gerard Bonavent et al It is certified that error appears in the above-identified patent and that said Letters Patent is hereby corrected as shown below:

Column 9, lines 25-26: reads "copolymer of which at least a part is dehydrogenated."

should read -- copolymer of which at least a part is hydrogenated. --

Column 10, line 25: reads "rioration thereof; said component being a film 40-200"

should read -- rioration thereof; said component being a film 50-200 --

Signed and Sealed this

Twenty-eighth Day of December 1982

[SEAL]

Attest:

GERALD J. MOSSINGHOFF

Attesting Officer

Commissioner of Patents and Trademarks